(12) United States Patent
Ganvir et al.

(10) Patent No.: US 11,008,406 B2
(45) Date of Patent: May 18, 2021

(54) METHOD FOR PREPARING CELLULOSE DOPE

(71) Applicant: Aditya Birla Science & Technology Company Private Limited, Mumbai (IN)

(72) Inventors: Vivek Ganvir, Mumbai (MH); Madan Kumar Singh, Mumbai (MH); Sachin Jadhav Gajanan, Mumbai (MH); Yogesh Shinde, Mumbai (MH); Shirish Thakre, Mumbai (IN)

(*) Notice: Subject to any disclaimer, the term of this patent is extended or adjusted under 35 U.S.C. 154(b) by 461 days.

(21) Appl. No.: 15/679,334

(22) Filed: Aug. 17, 2017

(65) Prior Publication Data

US 2017/0362342 A1    Dec. 21, 2017

(51) Int. Cl.
| | |
|---|---|
| *C08B 1/00* | (2006.01) |
| *C07C 69/88* | (2006.01) |
| *C07D 265/30* | (2006.01) |
| *C07D 233/54* | (2006.01) |
| *D01F 2/02* | (2006.01) |

(52) U.S. Cl.
CPC .............. *C08B 1/003* (2013.01); *C07C 69/88* (2013.01); *D01F 2/02* (2013.01); *C07D 233/54* (2013.01); *C07D 265/30* (2013.01); *C08J 2301/02* (2013.01)

(58) Field of Classification Search
CPC ......... C08B 1/003; C08J 2301/02; D01F 2/02
See application file for complete search history.

(56) References Cited

U.S. PATENT DOCUMENTS

| | | | | |
|---|---|---|---|---|
| 4,142,913 A | * | 3/1979 | McCorsley, III | C08B 1/003 106/200.3 |
| 5,702,515 A | * | 12/1997 | Urben | C08B 1/003 106/200.2 |
| 6,972,102 B1 | * | 12/2005 | Bauer | C08B 1/003 106/217.5 |
| 9,206,528 B2 | * | 12/2015 | Diener | D01D 1/065 |
| 10,612,191 B2 | * | 4/2020 | Moderl | D21C 9/005 |

* cited by examiner

*Primary Examiner* — Jeffrey M Wollschlager
(74) *Attorney, Agent, or Firm* — Finnegan, Henderson, Farabow, Garrett & Dunner, LLP

(57) ABSTRACT

The invention relates to a method for preparing a cellulose dope comprising mixing and dissolving the cellulosic raw material in dilute and concentrated aqueous organic solvent in a two-stage process to form a homogeneous slurry, followed by heating the homogeneous slurry to obtain a cellulose dope containing 11% to 20% cellulose by weight. The invention also relates to a cellulose dope comprising 11% to 20% cellulose by weight and 73% to 79% aqueous organic solvent wherein the concentration of the cellulosic and metallic impurities in the cellulose dope shows a percent reduction of 20% to 50% from the cellulosic raw material.

7 Claims, No Drawings

METHOD FOR PREPARING CELLULOSE DOPE

CROSS-REFERENCE TO RELATED PATENT APPLICATION

This application claims priority from Indian Patent Application No. 2016-21021087, filed Jun. 20, 2016. The entire contents of the above-referenced applications are expressly incorporated herein by reference.

FIELD OF INVENTION

The present invention relates to a cellulose dope. The present invention also relates to a method of preparing a cellulose dope.

BACKGROUND

Cellulosic fibers and other molded cellulose bodies such as filaments, foils and membranes are prepared by dissolving cellulosic raw materials in suitable solvent and then subsequently precipitating the dissolved cellulose in a suitable bath. One such method for obtaining molded cellulosic bodies is the amine oxide method. In the amine oxide method, a cellulosic raw material is dissolved in a solvent, consisting of an amine oxide such as N-Methylmorpholine-N-Oxide and water to obtain a cellulosic solution known as a cellulose dope. The cellulose dope is then precipitated in the desired shape in an aqueous precipitation bath to obtain the molded cellulosic bodies.

In the conventional process of obtaining the cellulose dope, cellulose or pulp sheets are added to a 65%-76% aqueous solution of N-Methylmorpholine-N-oxide (NMMO) such that the concentration of cellulose is between 9%-12%. The cellulose or pulp sheets are stirred in the NMMO solvent to allow the sheets to swell and disintegrate to form a homogenous slurry. Water is then evaporated from the homogenous slurry to obtain a cellulose dope that comprises 11% to 20% cellulose by weight and 73% to 76% of NMMO. It is necessary at slurry stage to have optimum pulp swelling and higher NMMO to cellulose ratio to achieve better uniformity of slurry for fast dissolution and homogeneous dope formation. To achieve this, in conventional processes, cellulose or pulp sheets are shredded to an optimum size before it is added to aqueous solution of NMMO. The shredding of the dried pulp requires intensive energy and raises safety concerns due to the cellulose dust explosion. This makes conventional processes for obtaining cellulose dope commercially and practically unviable.

US Publication number 2015/0007952 discloses an alternative method for preparation of cellulose dope. As per the disclosed method, a substantially dry cellulosic raw material is mixed with a suspending agent such as an aqueous NMMO solution in a slurrying unit, whereby a cellulose suspension with a cellulose content from 4.0 to 9.0% by weight is obtained. The cellulose suspension thus obtained is squeezed in a press to a cellulose content from 9% to 15% by weight to obtain suspending-agent-moistened cellulose. The suspending-agent-moistened cellulose is then further processed in a dissolution unit to obtain the cellulose dope. In the method disclosed excess NMMO obtained during the squeezing is recycled back to the slurrying unit. However, the method disclosed is operated at a relatively high temperature of 75 to 80 degree Celsius. Further the method disclosed does not allow for removal of impurities like hemicellulose and metal ions from the cellulose dope.

The impurities such as hemicellulose and metal ions causes the degradation of both cellulose and NMMO, which may lower the onset temperature of cellulosic dope and causes runaway reaction and thermal explosion during the dope preparation and fibre spinning.

The quantity of cellulosic raw material greater than 12% present in the cellulose suspension prepared in aqueous NMMO solution has an effect on the flowability and homogeneity of suspension which may lead to non-spinnable cellulose dope for manufacturing of fibers.

Thus, there is a need of an improved process for preparation of cellulose dope which avoids the drawbacks associated with the prior art processes. Specifically, there is a need for a process for preparation of cellulosic dope having lower impurities and higher cellulose content.

SUMMARY OF THE INVENTION

According to an embodiment of the invention, there is provided a method for preparing a cellulose dope comprising the steps of
  a) mixing cellulosic raw material and an anti-oxidant with 10% to 65% aqueous organic solvent by weight to obtain a slurry of 3% to 7% cellulose by weight;
  b) pressing the slurry obtained in step (a) to obtain a cellulose cake containing 30% to 65% cellulose by weight;
  c) shredding the cellulose cake obtained in step (b) and mixing the shredded cellulose cake and anti-oxidant with 76% to 88% aqueous organic solvent by weight to prepare a homogeneous slurry containing 9% to 20% cellulose by weight; and
  d) heating the homogeneous slurry obtained in step (c) at a temperature of 90 to 120 degree Celsius under vacuum to obtain cellulose dope containing 11% to 20% cellulose by weight.

According to another embodiment of the invention, there is provided a cellulose dope comprising.
11% to 20% cellulose by weight; and
73% to 79% aqueous organic solvent, wherein the concentration of the cellulosic and metallic impurities in the cellulose dope shows a percent reduction of 20% to 50% from the cellulosic raw material.

DETAILED DESCRIPTION

The present disclosure provides a method for the preparation of a cellulose dope.

The method of the present invention is adaptable by any cellulosic raw material. The cellulosic raw material may be bleached or unbleached pulp which can be made by various process of which Kraft, Prehydrolyzed Kraft or sulphite process is exemplary. Many other cellulosic raw materials, such as purified cotton linters, are also suitable.

The method for preparation of a cellulose dope comprises preparing a slurry of cellulose in an aqueous organic solvent by mixing a cellulosic raw material and an anti-oxidant with the aqueous organic solvent along with optional addition of water. The slurry of cellulose thus obtained is then further squeezed and pressed in a press to obtain a cellulose cake. The method further includes shredding the cellulose cake and adding said shredded cellulose cake along with the anti-oxidant to the aqueous organic solvent to obtain a homogenous slurry of cellulose in the organic solvent. Finally, the method further comprises heating the homogenous slurry of cellulose under vacuum to evaporate the excess water and to dissolve the cellulose in the organic solvent to obtain cellulose dope.

The aqueous organic solvent used in this method is selected from aqueous N-methylmorpholine-N-oxide (NMMO) or aqueous imidazolium based ionic liquids, wherein the cation moiety in the aqueous imidazolium based ionic liquids is N, N'-dialkyl substituted imidazolium and anionic groups such as alkanoates, halides, alkyl phosphates etc., and alkyl chains contain 1-20 carbon atoms. For both N, N'-alkyl substitution the alkyl group may be same or different. In a preferred embodiment, the aqueous organic solvent is aqueous N-Methylmorpholine-N-oxide (NMMO).

In step (a), there is 3% to 7% by weight of the cellulose to the total weight percent of the slurry. Moreover, this slurry is prepared using 10% to 65% weight of aqueous solution of organic solvent. On mixing these two, the cellulosic raw material swells and disintegrates in the organic solvent. The mixing of the cellulosic raw material, anti-oxidant and aqueous organic solvent is carried out at a temperature in the range of 50 to 70 degree Celsius for forming the cellulose slurry.

In step (a) and (c), the anti-oxidant added is propyl gallate. Propyl gallate is an essential ingredient in the method of preparation of the cellulose dope. The addition of propyl gallate with cellulose raw material and organic solvent is necessary and is done to prevent the formation of reactive radicals which subsequently cause the occurrence of chain reactions and possibly explosion. Propyl gallate also aids in maintaining the desired viscosity of the cellulose dope by averting the degradation of cellulose dope. Hence, the cellulose dope so formed can be spun to obtain cellulose fibers.

The cellulose slurry is squeezed and pressed in a press to prepare a cellulose cake, till the weight percent concentration of the cellulose in the cellulose cake is 30 to 65% of cellulose. This pressing of cellulose slurry is done by using a screw press, drum press or hydraulic press.

The cellulose cake obtained in this disclosed invention is cake showing reduction in the concentration of cellulosic and metallic impurities. The cellulose cake shows a percent reduction of 20% to 50% of both cellulosic and metallic impurities from the cellulose raw material. Here, the concentration of cellulosic impurities and metallic impurities is showing a reduction of about 20% to 25% and 20% to 50% respectively in the cellulose cake prepared in step (b). The cellulosic impurities mainly consists of hemicellulose while that of metallic impurities consists of metal ions, heavy metals, alkali metals and alkaline metals.

The shredding of cellulose cake is carried out using a simple shredder. The shredded cellulose cake and propyl gallate is added to 76% to 88% aqueous organic solvent to swell and dissolve the cellulosic raw material again, such that the percent weight of cellulose in cellulose dope is in a range of 9% to 20%. Preferably 76% to 88% of NMMO solution is used to dissolve the shredded cake. The shredded cellulose cake and organic solvent are then mixed to obtain the homogenous slurry. The shredded cellulose cake and NMMO are mixed at a temperature in the range of 65 to 80 degree Celsius to obtain the homogenous slurry.

Further the homogenous slurry is heated at temperature of 90 to 120 degree Celsius under vacuum of 50 to 100 mmHg to obtain the cellulose dope. Heating of the homogenous slurry allows excess water to evaporate and dissolves the cellulose in NMMO monohydrate to form the cellulose dope with desired cellulose concentration of 9% to 20% by weight.

In accordance with an embodiment of the present invention, the weight percent of the cellulose in the cellulose dope is in the range of 11% to 20% weight of cellulose. In accordance with an aspect, the cellulose dope comprises of 73% to 76% NMMO solution or aqueous imidazolium based ionic liquids.

Also, the NMMO rich filtrate obtained from the pressing of the cellulose slurry can be reused for preparation of the slurry of cellulose after it is passed through an ion exchange resin to remove impurities such as hemicellulose, metal ions, etc. The metallic impurities include metal ions, heavy metals, alkali metals and alkaline metals.

The method for preparing cellulosic dope disclosed in this invention can be employed for preparing of cellulose fibers. The process for obtaining cellulosic fibers involves spinning the cellulose dope so formed by the process disclosed, herein above by discharging the cellulose dope into air through a spinneret and submerging said discharged dope into a coagulation bath to form cellulosic fibres. The cellulosic fibres thus obtained are washed and dried.

The disclosed process enables the preparation of cellulose dope that contains lower impurities such as hemicellulose and metal ions as compared to the conventional process. Specifically, cellulose dope that is obtained from the disclosed process comprises about 20% to 50% of reduced concentration of hemicellulose and metal ions from the cellulosic raw material. It corresponds to about 20% reduction in the hemicellulose concentration and around 25% to 40% reduction in the metal ions concentration from that present in the initial raw material that is the cellulosic pulp. Thus, about 20% hemicellulose and 25% metal ion impurities are reduced in the slurry preparation stage.

Moreover the disclosed process allows preparation of cellulose dope with high cellulose content. Specifically, cellulose dope having up to 20% cellulose can be obtained using the disclosed process.

Further, as the method disclosed does not require shredding of cellulose raw material, the time required for dope preparation is shorter when compared to conventional methods. The process is economical. Additionally, the disclosed process allows improved swelling of cellulose which results in a homogeneous slurry having better flowability.

The following experimental examples are illustrative of the invention but not limitative of the scope thereof:

Example 1

124 g of ground dry cellulose pulp and 793 g of 76% NMMO aqueous solution and 0.351 gram of propyl gallate as anti-oxidant were mixed to form a cellulose slurry mixture containing 11.38% by weight cellulose, 66.54% of NMMO and 22.08% of water. The slurry was mixed in a sigma mixer as per Example 1 to get 900 g of cellulose dope with final proportion of 13% cellulose, 76% NMMO and 11% water. The cellulose dope so formed is further utilized to prepare cellulosic fibers and filaments. The cellulose dope is further spinned into air through a spinneret and submerging said discharged dope into a coagulation bath to form cellulosic fibres. The cellulosic fibres thus obtained are washed, dried and used for carrying out various analysis. This method of forming cellulose dope is the normal or the conventional method.

Example 2

127 grams of Saiccor pulp and 0.12 grams of propyl gallate and 2213 grams of 60% aqueous N-methylmorpholine-N-oxide (NMMO) solution are mixed to form a wet pulp slurry containing 0.1% propyl gallate, 5% cellulose, 57% of N-methylmorpholine-N-oxide and 38% of water. This slurry is mixed at a temperature of 60° C. in a glass or stainless steel (SS) vessel for a period of 15 minutes to form a slurry of 2340 grams. This hot slurry is transferred into a slurry press machine and the slurry is squeezed by applying 400 bar hydraulic pressure to remove excess NMMO. The slurry is pressed for few minutes at 400 bar pressure to form the cellulose cake. The NMMO which is squeezed is collected in a vessel.

Around 244 g of cake is obtained with composition of 48% cellulose, 31% NMMO and 21% water. This cellulose cake is further ground in a mixer for the second stage of the slurry preparation process. 244 grams of ground cellulose cake along with 0.234 grams of propyl gallate are mixed with 785 grams of 77.5% NMMO aqueous solution to form a cellulose slurry mixture containing 11.4% cellulose, 66.5% NMMO and 22.1% of water. The slurry is further heated and evaporated under vacuum to remove excess moisture and to obtain 900 g of cellulose dope with final proportion of 13% by weight of cellulose, 76% NMMO and 11% water. Further the method involves spinning the cellulose dope so formed by the process disclosed, herein above by discharging the cellulose dope into air through a spinneret and submerging said discharged dope into a coagulation bath to form cellulosic fibres. The cellulosic fibres thus obtained are washed, dried and used for carrying out various analysis.

Example 3

127 grams of Saiccor pulp and 0.12 grams of propyl gallate and 2213 grams of 50% aqueous N-methylmorpholine N-oxide (NMMO) solution are mixed to form a wet pulp slurry containing 0.1% propyl gallate, 5% cellulose, 47.5% of N-methylmorpholine N-oxide and 47.5% of water. This slurry is mixed at a temperature of 60° C. in a glass or stainless steel (SS) vessel for a period of 15 minutes to form a slurry of 2340 grams. This hot slurry is transferred into a slurry press machine and the slurry is squeezed by applying 400 bar hydraulic pressure to remove excess NMMO. The slurry is pressed for 5 minutes at 400 bar pressure to form the cellulose cake. The NMMO which is squeezed is collected in a vessel. The cellulose cake of around 212 grams is obtained with consistency of 55% cellulose by weight. This cellulose cake is further ground in a mixer for the second stage slurry preparation. 212 grams of ground cellulose cake along with 0.234 grams of propyl gallate are mixed with 817 grams of 78% NMMO aqueous solution to form a cellulose slurry mixture containing 11.4% cellulose, 66.5% NMMO and 22.1% of water. This mixture is heated up to 70° to 75° C. in a SS sigma mixer and the mixture is kept at this temperature for 15 minutes to make a homogeneous slurry. The homogeneous slurry is heated under vacuum of 50 Torr at a temperature of 105° C. followed by stirring the slurry at 40 rpm in a Sigma mixer for 90 minutes to evaporate water. At this stage, the cellulose is dissolved in concentrated NMMO solution to give 900 grams of cellulose dope with final portion of 13% cellulose, 76% NMMO and 11% water. Further the method involves spinning the cellulose dope so formed by the process disclosed, herein above by discharging the cellulose dope into air through a spinneret and submerging said discharged dope into a coagulation bath to form cellulosic fibres. The cellulosic fibres thus obtained are washed, dried and used for carrying out various analysis.

Furthermore the cellulose slurry, dope and the NMMO filtrate are tested for yield stress, pulp viscosity measurement and color and metal ions as shown below:

Table 1 shows the results for the yield stress, pulp viscosity measurement and color and metal ions tests conducted on the cellulose slurry and cellulose dope.

TABLE 1

| Physical properties analysis | Pulp | 5% Cellulose slurry | 11.3% Cellulose slurry | Dope |
|---|---|---|---|---|
| Yield stress, Pa | NA | 604 | 3600 | NA |
| Pulp viscosity, cP | 11.2 | 11.1 | 10.9 | 9.5 |
| Zero Shear Viscosity, PaS | NA | NA | NA | 2010 |

Table 2 shows the impurity mapping for the comparison of 2 stage slurry process versus conventional/normal process.

TABLE 2

| Impurity Analysis | Fresh Pulp | 60% NMMO | 2 stage slurry process | | | | Normal process | |
|---|---|---|---|---|---|---|---|---|
| | | | Return NMMO | Cake | Dope | Spin Bath | Dope | Spin Bath |
| Yellowness Index | NA | 1.0 | 16.7 | NA | 80 | 18 | 87 | 25 |
| Hemicellulose wrt pulp, % | 3.0% | 0 | 0.7% | 2.3% | 2.3% | 0.8% | 3.0% | 1.5% |
| Metallic impurity by ICP | | | | | | | | |
| Calcium, ppm | 45 | 1.8 | 3.6 | 32 | 18.1 | 2 | 22.2 | 6.3 |
| Iron, ppm | 6 | 0.5 | 1 | 4 | 2.6 | 0.5 | 4.9 | 1.8 |
| Sodium, ppm | 412 | 10.8 | 17 | 278 | 51.3 | 12 | 59.7 | 18.3 |
| Potassium, ppm | 21 | 1.2 | 3 | 15 | 3.3 | 2 | 2.3 | 3.8 |
| Magnesium, ppm | 4 | 0.5 | 1.8 | 3 | 2.2 | 1 | 1.7 | 3.3 |

Here, % Hemicellulose removal=(pulp Hemicellulose−Hemicellulose in cake)/Pulp Hemicellulose Hence, % Hemicellulose removal=(3−2.3)/3=23%

% Metal ion removal=(metals in pulp−metals in cake)/metals in pulp

Thus, % Metal ion removal=(491−326)/491=33.6%

The above tests show the percent reduction occurring in the concentration of hemicellulose and metal ions from the cellulosic raw materials that is the Saiccor pulp in case of example 3.

Example 4

The steps of Example 3 were repeated to prepare the cellulose dope, however, replacing 50% NMMO with 25% NMMO in this case. Other parameters of the method are kept same as in Example 1. Around 189 g of cake is obtained with composition of 62% cellulose, 9.5% NMMO and 28.5% water. This wet cake is ground in a mixer for second stage slurry and cellulose dope preparation. 189 g of ground wet cake, 844 g of 79% NMMO aqueous solution and 0.234 g of propyl gallate as anti-oxidant were mixed to form a cellulose slurry mixture containing 11.38% cellulose, 66.54% of NMMO and 22.08% of water. The slurry was mixed in a sigma mixer as per Example 1 to get 900 g of cellulose dope with final proportion of 13% cellulose, 76% NMMO and 11% water.

The dope was further spun by air gap spinning method at 20 mm air gap method and cellulose fibers were produced.

Example 5

The steps of Example 3 were repeated to prepare the cellulose dope, however, with a change in the temperature of 5% slurry preparation from 60° C. to 50° C. All other parameters of the method were kept the same as in Example 1. Around 202 g of cake was obtained with composition of 58% cellulose, 21% NMMO and 21% water.

This wet cake was ground in a mixer for second stage slurry and cellulose dope preparation.

202 g of ground wet cake, 825 g of 78% NMMO aqueous solution and 0.234 g of propyl gallate as anti-oxidant were mixed to form a cellulose slurry mixture containing 11.38% cellulose, 66.54% of NMMO and 22.08% of water. The slurry, was mixed in a sigma mixer as per Example 1 to get 900 g of cellulose dope with final proportion of 13% cellulose, 76% NMMO and 11% water. Further the method involves spinning the cellulose dope so formed by the process disclosed, herein above by discharging the cellulose dope into air through a spinneret and submerging said discharged dope into a coagulation bath to form cellulosic fibres. The cellulosic fibres thus obtained are washed, dried and used for carrying out various analysis.

Example 6

The steps of Example 3 were repeated to prepare the cellulose dope, however, with a change in the pressing condition of 5% slurry from 400 bar to 200 bar. All other parameters of the method were kept same as in Example 1 Around 249 g of cake was obtained with composition of 47% cellulose, 26.5% NMMO and 26.5% water. This wet cake was ground in a mixer for second stage slurry and cellulose dope preparation.

249 g of ground wet cake and 793 g of 78% NMMO aqueous solution and 0.234 g of propyl gallate as anti-oxidant were mixed to form a cellulose slurry mixture containing 11.38% cellulose, 66.54% of NMMO and 22.08% of water. The slurry was mixed in a sigma mixer as per Example 1 to get 900 g of cellulose dope with final proportion of 13% cellulose, 76% NMMO and 11% water. Following this, the method includes spinning the cellulose dope so formed by the process disclosed, herein above by discharging the cellulose dope into air through a spinneret and submerging said discharged dope into a coagulation bath to form cellulosic fibres. The cellulosic fibres thus obtained are washed, dried and used for carrying out various analysis.

Example 7

The process steps of Example 3 to form the cellulose dope were repeated in this case, keeping all the parameters the same except the slurry was prepared with 5 times recycled 50% aqueous NMMO solution. A 212 g of cellulose cake was obtained with consistency of 55% cellulose by weight. This wet cake was ground in a mixer for second stage slurry and cellulose dope preparation. The second stage slurry and cellulose solution in NNMO was made according to the procedure described in Example 3.

Further the method involves spinning the cellulose dope so formed by the process disclosed, herein above by discharging the cellulose dope into air through a spinneret and submerging said discharged dope into a coagulation bath to form cellulosic fibres. The cellulosic fibres thus obtained are washed, dried and used for carrying out various analysis.

Results of the analysis carried out on the cellulose dope to determine the percent of solid cellulose present in the cellulose dope prepared in Examples 1 to 6 and the mechanical properties of the cellulose slurry, dope and cellulose fibers in Examples 1 to 7 are summarized as below:

Table 3 shows the percent of solid cellulose present in the cellulose dope prepared in the Examples 2 to 7

TABLE 3

| Example No. | Slurry consistency, % | NMMO Conc. % | Temp. of slurry ° C. | Hydraulic Pressure, bar | % Solid after pressing |
|---|---|---|---|---|---|
| 2 | 5 | 60 | 60 | 400 | 48 |
| 3 | 5 | 50 | 60 | 400 | 55 |
| 4 | 5 | 25 | 60 | 400 | 62 |
| 5 | 5 | 50 | 50 | 400 | 58 |
| 6 | 5 | 50 | 60 | 200 | 47 |
| 7 | 5 | 5 times recycled 50% | 60 | 400 | 55 |

Table 4 shows the mechanical properties of the cellulose slurry, dope and fiber for all the Examples 1 to 7

TABLE 4

| | Slurry Yield stress, Pa | | Dope, | | Fiber Properties | | |
|---|---|---|---|---|---|---|---|
| Example No | 5% cellulose | 11.3% cellulose | ZSV, Pa S | Yellow Index | Denier | Tenacity, gpd | Elongation, % |
| 1 (Normal Dope) | NA | 3750 | 2080 | 89 | 1.23 | 4.45 | 8.80 |
| 2 | 650 | 3680 | 2010 | 80 | 1.27 | 4.63 | 10.20 |

TABLE 4-continued

| | Slurry Yield stress, Pa | | Dope, | | Fiber Properties | | |
|---|---|---|---|---|---|---|---|
| Example No | 5% cellulose | 11.3% cellulose | ZSV, Pa S | Yellow Index | Denier | Tenacity, gpd | Elongation, % |
| 3 | 760 | 3710 | 1960 | 82 | 1.29 | 4.54 | 9.30 |
| 4 | 470 | 3780 | 1890 | 78 | 1.24 | 4.42 | 9.90 |
| 5 | 604 | 3690 | 1830 | 79 | 1.35 | 4.57 | 11.90 |
| 6 | 630 | 3720 | 1940 | 82 | 1.27 | 4.29 | 10.20 |
| 7 (Recycled 50% NMMO) | 604 | 3620 | 1910 | 81 | 1.24 | 4.49 | 10.40 |

Table 5 shows the comparison chart of the cellulose dope formed by normal conventional method and two-stage slurry preparation method with recycled NMMO and fresh NMMO

TABLE 5

| | 2 stage process | | | 2 stage process 5 time recycled NMMO | | | Normal process | |
|---|---|---|---|---|---|---|---|---|
| Impurity Analysis | Return NMMO | Dope | Spin Bath | 5 cycle NMMO | Dope | Spin Bath | Dope | Spin Bath |
| Yellowness Index | 16.7 | 80 | 18 | 41.7 | 81 | 31 | 87 | 25 |
| Hemicellulose wrt pulp, % | 0.7% | 2.3% | 0.8% | 0.9% | 2.70% | 0.80% | 3.0% | 1.5% |
| Metallic impurity by ICP | | | | | | | | |
| Calcium, ppm | 3.6 | 18.1 | 2 | 6.6 | 12.7 | 8.4 | 22.2 | 6.3 |
| Iron, ppm | 1 | 2.6 | 0.5 | 1.0 | 7.1 | 1.5 | 4.9 | 1.8 |
| Sodium, ppm | 17 | 51.3 | 12 | 26.0 | 46.0 | 22.6 | 59.7 | 18.3 |
| Potassium, ppm | 3 | 3.3 | 2 | 3.0 | 1.1 | 3.0 | 2.3 | 3.8 |
| Magnesium, ppm | 1.8 | 2.2 | 1 | 1.3 | 3.1 | 2.3 | 1.7 | 3.3 |

The cellulose dope so obtained from the present invention shows various properties. The cellulose dope obtained through the two-stage slurry preparation process comprises of a dope with lesser concentration of metallic and hemicellulose impurities due the tendency of both cellulosic and hemicellulosic impurities to dissolve in dilute aqueous organic solvent. The impurities so dissolved in the organic solvent are removed with the organic solvent filtrate during the pressing step. Further the two-stage slurry preparation method disclosed in this disclosure aids to form a cellulose dope with much higher amount of organic solvent into the cellulosic polymer chain structure leading to a cellulose dope with desired viscosity, efficient spinning ability and uniform cellulose fibers without of any sign of patchiness through the fiber's length. This two stage slurry process also helps in forming a homogeneous blend of the cellulose slurry and dope thus facilitating the production cellulose fibers with unvarying and consistent mechanical and chemical properties. Further, the fibres obtained by using the disclosed dope and the disclosed method can be used for tire chord application and also find application in composites where strength is the main criteria.

The above examples are non-limiting. The invention is defined by the claims that follow.

We claim:

1. A method for preparing a cellulose dope comprising the steps of:
    a) mixing cellulosic raw material and an anti-oxidant with 10% to 65% aqueous organic solvent by weight of aqueous solution of N-methylmorpholine-N-oxide (NMMO) to obtain a slurry of 3% to 7% cellulose by weight of the slurry;
    b) pressing the slurry obtained in step (a) to obtain a cellulose cake containing 30% to 65% cellulose by weight;
    c) shredding the cellulose cake obtained in step (b) and mixing the shredded cellulose cake and said anti-oxidant with 76% to 88% aqueous organic solvent by weight of aqueous solution of N-methylmorpholine-N-oxide (NMMO) to prepare a homogeneous slurry containing 9% to 20% cellulose by weight of the homogeneous slurry; and
    d) heating the homogeneous slurry obtained in step (c) at a temperature of 90 to 120 degree Celsius under vacuum to obtain cellulose dope containing 11% to 20% cellulose by weight.

2. The method as claimed in claim 1, wherein the aqueous organic solvent further comprises aqueous imidazolium based ionic liquids.

3. The method as claimed in claim 1, wherein the concentration of cellulosic impurities in the cellulosic raw materials shows a percent reduction of 20% to 25% and metallic impurities shows a percent reduction of 20% to 50% in the cellulose cake of step (b).

4. The method as claimed in claim 1, wherein the anti-oxidant is propyl gallate.

5. The method as claimed in claim 1, wherein the cellulosic raw material, the anti-oxidant and the aqueous solution are mixed in step (a) at a temperature of 50 to 70 degree Celsius.

6. The method as claimed in claim 1, wherein the pressing of slurry is carried out using a press selected from a screw press, a drum press or a hydraulic press.

7. The method as claimed in claim 1, wherein the cellulosic dope obtained in step (d) comprises 73% to 79% by weight of N-Methylmorpholine-N-oxide (NMMO).

* * * * *